United States Patent [19]

Nelson

[11] 4,310,525
[45] Jan. 12, 1982

[54] METHOD OF TREATMENT OF INFLAMMATION

[75] Inventor: Eric L. Nelson, Santa Ana, Calif.

[73] Assignee: Nelson Research & Development Company, Irvine, Calif.

[21] Appl. No.: 227,628

[22] Filed: Jan. 23, 1981

[51] Int. Cl.³ .............................................. A61K 31/33
[52] U.S. Cl. .................................................... 424/244
[58] Field of Search ........................................ 424/244

[56] References Cited

U.S. PATENT DOCUMENTS 3,989,816  11/1976  Rajadhyaksha ..................... 424/60

Primary Examiner—Stanley J. Friedman
Attorney, Agent, or Firm—Martin A. Voet

[57] ABSTRACT

There is disclosed a method of treatment of inflammation in humans and animals comprising contacting the inflamed area with an effective, anti-inflammatory amount of 1-dodecylazacycloheptan-2-one.

13 Claims, No Drawings

METHOD OF TREATMENT OF INFLAMMATION

BACKGROUND OF THE INVENTION

1. Field of the Invention

The invention relates generally to a method of treatment of inflammation. More particularly the invention relates to a method of treatment of inflammation topically in humans and animals with 1-dodecylazacycloheptan-2-one.

2. Background of the Prior Art

Inflammation, or the "inflammatory response," is the net result of interconnected physiological events, including increased vascular permeability, fluid accumulation, and the migration of a changing population of inflammatory cells into the inflamed area. The clinical manifestations of inflammation include swelling, increased local temperature, erythema and pain. The inflammatory response can be triggered by any of a number of causative factors, including certain bacteria, heat, radiation, hypersensitivity to chemical agents and the like. The inflammatory response is generally believed to be a primary defense mechanism in the body, but unchecked, can become excessive resulting in functional impairment.

A variety of dermatoses, including acne and acne-like conditions, are accompanied by inflammation which is substantially localized in the tissues immediately surrounding the acne or acne-like comedones and lesions. Inflammation accompanying such dermatoses can cause the functional impairment of sub-epidermal glandular tissue and ultimately result in gross anatomic damage to the skin, i.e., scar tissue and pitting.

Burns, including actinic erythema and contact burns, and insect bites constitute other well-recognized causative factors which trigger the inflammatory response in humans and other animals.

The variety of means for use in the treatment of inflamed tissue underlines the need for safe and effective topical compositions of the present type. Many age-old compositions such as cocoa butter are merely palliatives which lubricate and soothe inflamed tissue. More recently, topical anesthetics have been added to moisturizing creams and bases to help alleviate the pain which often accompanies the inflammatory response. Steroidal and antihistamine preparations have been applied to inflamed tissue. Various detergent and bactericidal compositions have been suggested for the treatment of acne and other dermatoses.

U.S. Pat. No. 3,989,816 discloses a vehicle composition containing 1-substituted azacycloheptan-2-ones useful in enhancing penetration of the skin of physiologically active agents. British Pat. No. 1,553,309 discloses 1-dodecylazacycloheptan-2-one as a penetration enhancer, though no therapeutic activity of the 1-dodecylazacycloheptan-2-one per se is disclosed.

SUMMARY OF THE INVENTION

I have now discovered that 1-dodecylazacycloheptan-2-one has utility itself in the treatment of inflammation associated with inflammatory disorders and conditions such as, for example, common skin disorders such as psoriasis, dermatitis and eczema, insect bite, pruritis, edema, burns, acne and arthritis.

More specifically, this invention relates to a method of temporarily reducing the signs and symptoms of inflammation in humans and animals comprising contacting the inflamed area with an effective, anti-inflammatory amount of 1-dodecylazacycloheptan-2-one.

The invention further relates to a method of treating inflammation in humans and animals comprising topically treating the inflamed area with a composition comprising at least about 10% 1-dodecylazacycloheptan-2-one.

DETAILED DESCRIPTION OF THE INVENTION 1-dodecylazacycloheptan-2-one is a clear, colorless liquid having a boiling point of 160° C. at 50 $\mu$Hg. It is miscible with most organic solvents including hydrocarbons, alcohols and ketones and is immiscible with water. It has an acute oral toxicity of 8 gms/kg ($LD_{50}$ rat). Its method of manufacture is disclosed in British Pat. No. 1,553,309 which disclosure is herein incorporated by this reference.

The amount of 1-dodecylazacycloheptan-2-one that may be used in the invention varies with the inflammatory condition being treated, the patient, the location of the inflammation and the concentration of 1-dodecylazacycloheptan-2-one that is desired. Generally, the compound is used with conventional pharmaceutical carriers and in conventional dosage forms when used at less than 100% concentration.

Dosage forms for topical application may include solutions, nasal sprays, lotions, ointments, creams, gels, suppositories, sprays, aerosols and the like. Typical conventional pharmaceutical carriers which make up the foregoing dosage forms include acetone, isopropyl alcohol, ethyl alcohol, polyvinyl pyrrolidone, propylene glycol, fragrances, gel-producing materials, mineral oil, stearyl alcohol, stearic acid, spermaceti, sorbitan monooleate, "Polysorbates", "Tweens", sorbital, methylcellulose, etc.

The concentration of 1-dodecylazacycloheptan-2-one which may be used in the invention varies from about 10% to 100% and preferably about 40% to about 80% by weight.

The method of treatment is generally topical treatment of a suitable dosage form as hereinbefore described to the affected area 1 to 4 times daily until the inflammation has been reduced or eliminated.

Inflamed tissue is treated by applying thereto a safe and effective amount of an anti-inflammatory composition of the foregoing type. Such inflamed tissue can comprise, for example, acne or acne-like comedones and lesions, and the tissue adjacent thereto, inflamed tissue accompanying minor burns, inflamed tissue which is the product of insect bites, inflamed tissue which is the product of hypersensitivity to a chemical or biological agent, and the like. It will be appreciated that the course of treatment of an inflamed area will vary somewhat, depending on the type of inflammation involved. For example, when treating acne or inflammation caused by other types of dermatoses, a treatment regimen involving multiple applications over a course of days or weeks will be involved. Conversely, when treating burns or insect bites, one or two applications of the anti-inflammatory composition will have to suffice in order to provide the immediate benefits desired by the user. Adjustment of concentration levels and usage rates according to the application regimen should preferably be considered.

When treating acne or acne-like lesions and comedones, it is preferred that a regimen involving multiple applications of the composition over a period of days or weeks be employed. Accordingly, it is preferred that sufficient composition to provide 1-dodecylazacycloheptan-2-one at the rate of from about 0.3 milligrams per square centimeter (mg/cm$^2$) to about 3 mg/cm$^2$ of treated tissue be applied in each treatment.

When treating burned tissue, inflamed tissue which is the product of an insect bite, or inflamed tissue which is the product of hypersensitivity to a chemical or biological agent, it is preferred that sufficient composition to provide 1-dodecylazacyloheptan-2-one at the rate of about 0.4 mg/cm$^2$ to about 4 mg/cm$^2$ of treated tissue be applied in each treatment. Accordingly, compositions for such occasional use regimens will contain up to about 100% by weight of the 1-dodecylazacyloheptan-2-one.

As used herein, the term "topical" is intended to include application to all external membrane barriers including the cutaneous or epidermis regions and the mucous membranes including the gastrointestinal tract, the respiratory tract and the genitourinary tract.

As used herein, the term "treating inflammation" means "temporarily reducing the signs and symptoms of inflammation."

The examples which follow illustrate the invention, but are not intended as limitations on its scope.

EXAMPLE I

Preparation of 1-dodecylazacycloheptan-2-one

The operation was carried out under nitrogen. In a 5 liter 3-neck flask equipped with an efficient condenser, an additional funnel and a mechanical stirrer was placed 91.8 g (1.91 M) of 50% sodium hydride (dispersed in mineral oil). This was mixed with 600 ml of pet. ether (30–60), the mixture was momentarily stirred and then sodium hydride was allowed to settle. Most of the petroleum ether was pipetted out and 1500 ml of toluene was added to the NaH. To this was added under stirring and dropwise a solution of 180 g (1.59 M) of azacycloheptan-2-one in 800 ml of toluene. Foaming, hydrogen evaluation and formation of sodium salt took place. After the addition, the reaction mixture was refluxed for two hours and then cooled to room temperature. A solution of 398 g (1.59 M) of 1-bromododecane in 100 ml of toluene was added dropwise under stirring. Upon completion of the addition, the reaction mixture was refluxed for 45 hours. After cooling, the contents were filtered through celite and the filtrate was concentrated to a yellow oil. This was distilled at 155° to 160°/100μ to give 402 g (89%) of a clear colorless oil. Redistillation at 155° to 160°/100μ gave 396 g (88.5%) of pure 1-dodecylazacycloheptan-2-one.

EXAMPLE II

The following formulations were prepared:

|  | A | B | C | D | E |
|---|---|---|---|---|---|
| 1-dodecylazacycloheptan-2-one | 10 | 30 | 50 | 60 | 80 |
| Propylene Glycol | 90 | — | 15 | — | — |
| Cetyl Alcohol | — | — | 20 | — | — |
| Sodium Lauryl Sulfate | — | — | 15 | — | — |
| Polyethylene Glycol 400 | — | — | — | 39.86 | — |
| Carboxyvinyl Polymer Powder | — | — | — | 0.10 | — |
| Triethanolamine | — | — | — | 0.04 | — |
| Polyethylene Glycol 4000 | — | 55 | — | — | — |
| Propylene Glycol Monostearate | — | 15 | — | — | — |
| Carbo Wax 1500 | — | — | — | — | 15 |
| Ethanol | — | — | — | — | 5 |

Formulation A-Liquid

The 1-dodecylazacycloheptan-2-one is combined with propylene glycol and is useful where a liquid is the dosage form.

Formulation B-Suppository

The solid constituents are melted and added to the 1-dodecylazacycloheptan-2-one and poured into an appropriate mold. The product is useful for rectal or vaginal application.

Formulation C-Lotion

The 1-dodecylazacycloheptan-2-one is added to a stirred, cooling melt of the other ingredients. The preparation is particularly useful for the treatment of inflamed dermatoses by topical application to the affected skin area.

Formulation D-Ointment (Gel)

The polyethylene glycol 400 and 1-dodecylazacycloheptan-2-one are combined and the carboxy vinyl polymer gelling agent is sprinkled on the surface of the combined liquids and stirred until all of the particles have been melted and dispersed. The triethanolamine is then added dropwise to the mixture until it has gelled. This gel is particularly effective in the treatment of seborrhea and other scalp and hair inflammatory conditions.

Formulation E-Ointment

An ointment is prepared by blending the indicated ingredients. The dosage may be applied topically or sublingually.

EXAMPLE III

A. Formulation C of Example II is applied directly to the inflamed tissue associated with acne lesions. The applications are 2 to 3 times daily for two weeks. A decrease in inflammation of the skin with attendant cosmetic advantages to the user is noted.

B. A thin layer of Formulation A of Example II is applied to inflamed skin resulting from sunburn. A decrease in redness and pain is noted over a six hour period.

C. A thin layer of Formulation D is spread over a small layer of skin which has been inflamed by mosquito bites. The inflammation is substantially reduced and the swelling and sensation of itching and pain is substantially relieved.

I claim:

1. A method of treating inflammation in humans and animals comprising contacting the inflamed area of said humans and animals with an effective, anti-inflammatory amount of 1-dodecylazacycloheptan-2-one as the sole active anti-inflammatory agent.

2. The method of claim 1 wherein the inflammation results from arthritis.

3. The method of claim 1 wherein the inflammation results from psoriasis.

4. The method of claim 1 wherein the inflammation results from seborrheic dermatitis.

5. The method of claim 1 wherein the inflammation results from eczema.

6. The method of claim 1 wherein the inflammation results from pruritis.

7. The method of claim 1 wherein the inflammation results from edema.

8. The method of claim 1 wherein the inflammation results from insect bite.

9. The method of claim 1 wherein the inflammation results from a burn.

10. The method of claim 1 wherein an effective amount ranges between about 10% to 100% by weight.

11. The method of claim 1 wherein an effective amount ranges between about 40% to about 80% by weight.

12. A method of treating inflammation in humans and animals comprising topically treating the inflamed area with a composition comprising at least about 10% 1-dodecylazacycloheptan-2-one.

13. The method of claim 12 wherein the composition consists essentially of 1-dodecylazacycloheptan-2-one.

* * * * *